United States Patent [19]
Schwabe et al.

[11] Patent Number: 5,811,395
[45] Date of Patent: Sep. 22, 1998

[54] RELAXIN ANALOGS AND DERIVATIVES METHODS AND USES THEREOF

[75] Inventors: Christian Schwabe, Charleston, S.C.; Elaine Unemori, Oakland, Calif.

[73] Assignees: Medical University of South Carolina, Charleston, S.C.; Connetics Corporation, Palo Alto, Calif.

[21] Appl. No.: 483,476

[22] Filed: Jun. 7, 1995

[51] Int. Cl.$^6$ .......................... A61K 38/16; A61K 38/17; C07K 7/10
[52] U.S. Cl. .............................. 514/12; 514/21; 330/399; 330/324
[58] Field of Search ...................................... 530/399, 324; 514/12, 21

[56] References Cited

U.S. PATENT DOCUMENTS

| 5,023,321 | 6/1991 | Hudson et al. | 530/324 |
| 5,166,191 | 11/1992 | Cronin et al. | 514/12 |
| 5,179,195 | 1/1993 | Hudson et al. | 530/324 |
| 5,451,572 | 9/1995 | Cipolla et al. | 514/21 |
| 5,478,807 | 12/1995 | Cronin et al. | 514/12 |

OTHER PUBLICATIONS

Bani et al., 1994, "Differentation of breast cancer cells in vitro is promoted by the concurrent influence of myoepithelial cells and relaxin," *Bio J. Cancer* 70:900–904.
Bryant–Greenwood, 1982, *Endocrine Reviews* 3:62–90.
Bullesbach and Schwabe, 1991, *J. Biol. Chem.* 266:10754–10761.
Burkhardt et al., 1994, *Genomics* 20:13–19.
Osheroff et al., 1990, *The Journal of Biological Chemistry* 265:9396–9401.
Stemmermann et al., 1994, *Journal of Endocrinology* 140:321–325.

*Primary Examiner*—Douglas W. Robinson
*Assistant Examiner*—P. Lynn Touzeau
*Attorney, Agent, or Firm*—Pennie & Edmonds LLP

[57] ABSTRACT

The present invention relates to a relaxin analogs and derivatives, and uses thereof. The present invention further relates to compositions comprising a relaxin analogs and derivatives, and relaxin wherein such composition exhibits an additive or synergistic effect.

8 Claims, 1 Drawing Sheet

FIGS. 1A and 1B

RELAXIN ANALOGS AND DERIVATIVES METHODS AND USES THEREOF

A portion of the work set forth herein was supported by grants NIHGMS-48893 and NSF MCB-9406656 and by the Medical University of South Carolina.

1. INTRODUCTION

The present invention relates to relaxin analogs, and uses thereof. The present invention further relates to compositions and formulations comprising relaxin analogs and their uses. The present invention also relates to compositions and formulations comprising the relaxin analogs, its derivatives and/or relaxin or other agent wherein such composition exhibits an additive or synergistic effect.

2. BACKGROUND OF THE INVENTION

A family of hormones, comprising insulin, insulin-like growth factors (I and II), bombyxin, molluscan insulin-related peptide and relaxin, has been identified and designated as "insulin-related." Blundell and Humbel, 1980, Nature 287:781–787; Büllesbach and Schwabe, 1991, J. Biol. Chem. 266:10754–10761. The proteins comprising this family of hormones represents a group of polypeptides having homologous primary and secondary structure but divergent biological functions.

Relaxin has been purified from a variety of species including porcine, murine, equine, shark, tiger, rat, dogfish and human. In the human, relaxin is most abundantly found in the corpus lutea (CL) of pregnancy. Mature human relaxin is a hormonal peptide of approximately 6000 daltons which facilitates the birth process by remodelling the reproductive tract before parturition. More specifically, relaxin appears to modulate the restructuring of connective tissues in target organs to obtain the required changes in organ structure during pregnancy and parturition. See, Hisaw, 1926, Proc. Soc. Exp. Biol. Med. 23:661–663; Schwabe, et al., 1977, Biochem. Biophys. Res. Comm. 75:503–570; James, et al., 1977, Nature, 267:544–546. A concise review of relaxin was provided by Sherwood, D. in The Physiology of Reproduction, Chapter 16, "Relaxin", Knobil, E. and Neill, J., et al. (eds.), (Raven Press Ltd., New York), pp. 585–673 (1988).

While predominantly a hormone of pregnancy, relaxin has also been detected in the non-pregnant female as well as in the male. Bryant-Greenwood, 1982, Endocrine Reviews 3:62–90; Weiss, 1984, Ann. Rev. Physiol. 46:43–52.

Two human gene forms encoding for human relaxin have been identified, (H1) and (H2). Hudson, et al., 1983, Nature 301 628–631; Hudson, et al., 1984, EMBO J., 3:2333–2339; and U.S. Pat. Nos. 4,758,516 and 4,871,670. Only one of the gene forms (H2) has been found to be transcribed in CL. When synthetic human relaxin (H2) and certain human relaxin analogs were tested for biological activity, the tests revealed a relaxin core necessary for biological activity as well as certain amino acid substitutions for methionine that did not affect biological activity. Johnston, et al., in Peptides: Structure and Function, Proc. Ninth American Peptide Symposium, Deber, C. M., et al. (eds.) (Pierce Chem. Co. 1985). As set forth in U.S. Pat. No. 5,166,191, the binding activity of native relaxin has been calculated to have a $K_D$ of about 1.3 nM (measure in uterus) or 1.37 (measured in normal heart).

Methods of making relaxin are described in U.S. Pat. No. 4,835,251 and in co-pending U.S. Ser. Nos. 07/908,766 (PCT US90/02085) and 08/080,354 (PCT US94/0699). Methods of using relaxin in cardiovascular therapy and in the treatment of neurodegenerative diseases are described in U.S. Pat. No. 5,166,191 and in U.S. Ser. No. 07/902,637 (PCT US92/06927). Certain formulations of human relaxin are described in allowed U.S. Ser. No. 08/050,745.

In view of the diverse applications for relaxin currently being explored, identification of relaxin analogs retaining or having higher biological activity has been the focus of investigation. Until the present invention, however, a substantially biologically active analog of relaxin had not been identified.

3. SUMMARY OF THE INVENTION

The present invention is directed to synthesized or recombinant compositions derived from the deduced amino acid and nucleic acid sequences of naturally-occurring human relaxin and derivatives thereof. In one embodiment of the present invention, the composition comprises the full-length amino acid sequence of the relaxin wherein Glu has been substituted by Asp at the B14 position. In another embodiment of the present invention, the composition comprises one or more relaxin B14 analog protein derivatives, wherein the protein is shortened at either or both its 3' and 5' ends of either or both the A and B chains. In yet further embodiments of the present invention, the composition is radiolabelled and comprises a full-length relaxin analog or a derivative thereof.

The present invention is further directed to the use of such compounds for the treatment of diseases and disorders which may be otherwise treated with relaxin, either alone, or in combination with relaxin or another agent, and formulations thereof. In one embodiment of the present invention, the diseases or disorders are related to the abnormal expression of collagen and/or fibronectin. More specifically, such diseases or disorders include scleroderma. In another embodiment of the present invention, the diseases and/or disorders are more generally related to the activation of one or more biological functions as a result of binding with the relaxin receptor. Such diseases and/or disorders can include cardiovascular disease, sinus bradycardia, neurodegenerative or neurologic disease, depression and hair loss.

The present invention is also related to the use of relaxin analogs, whether labelled or unlabelled, as a tracer which could then be used to separate by HPLC the different relaxin analog derivatives to yield a carrier-free tracer, in binding assays, and for relaxin receptor mapping.

4. DEFINITIONS

As used in the present specification, the following words and phrases are generally intended to have the meanings as set forth below, except to the extent that the context in which they are used indicates otherwise.

The term "relaxin" means human relaxin, including full length relaxin or a portion of the relaxin molecule that retains biological activity [as described in U.S. Pat. No. 5,023,321, preferably recombinant human relaxin (H2)] and other active agents with relaxin-like activity, such as agents that competitively displace bound relaxin from a receptor. Relaxin can be made by any method known to those skilled in the art, preferably as described in U.S. Pat. No. 4,835,251 and in co-pending U.S. Ser. Nos. 07/908,766 (PCT US90/02085) and 08/080,354 (PCT US94/0699).

The term "relaxin analog," unless stated otherwise, refers to the Asp(B14) analog and derivatives thereof, including full length Asp(B14) relaxin or a portion of the Asp(B14) relaxin molecule that retains biological activity [as described in U.S. Pat. No. 5,023,321, preferably recombinant human relaxin (H2)] and other active agents with relaxin-like activity, such as agents that competitively displace bound relaxin from a receptor.

5. DETAILED DESCRIPTION OF THE INVENTION

5.1. Structure and Activity of Relaxin Analogs

The full-length B-chain of relaxin analog Asp(B14) wherein glutamic acid at position 14 of the B-chain has been replaced by an aspartic acid has the amino acid sequence set forth below as SEQ. ID 1.:

SEQ. ID 1

| 1 | 2 | 3 | 4 | 5 | 6 | 7 | 8 | 9 | 10 |
|---|---|---|---|---|---|---|---|---|---|
| H—Asp— | Ser— | Trp— | Met— | Glu— | Glu— | Val— | Ile— | Lys— | Leu— |
| 11 | 12 | 13 | 14 | 15 | 16 | 17 | 18 | 19 | 20 |
| Cys— | Gly— | Arg— | Asp— | Leu— | Val— | Arg— | Ala— | Gln— | Ile— |
| 21 | 22 | 23 | 24 | 25 | 26 | 27 | 28 | 29 | |
| Ala— | Ile— | Cys— | Gly— | Met— | Ser— | Thr— | Trp— | Ser— | OH |

Derivatives of such analog are preferably comprised of a shortened A-chain and/or B-chain, at either the 5' or 3' end of the molecule, wherein the amino acids at positions B13 (an arginine) through B17 (an arginine) are retained. Preferably, the A-chain is shortened up to about 6 amino acids, at either or both the 5' and 3' ends of said chain and the B-chain is shortened up to about 5 amino acids at either or both the 5' and 3' ends of said chain. Identification of other relaxin analogs and derivatives may be obtained using known techniques and this structural information regarding relaxin.

A basis for the present invention is the inventors' unexpected development of relaxin analogs that can exhibit higher biological activity and higher physiological affinity than the previously identified relaxins. More specifically, in previous studies, it has been observed that the arginines for human relaxin at positions B13 and B17 and potentially the amino acids between such arginines and of the first helix turn in the midregion of the B-chain (Arg-Glu-Leu-Val-Arg) are necessary or important to relaxin activity. Thus, it was believed that additions, deletions or substitutions to such regions could result in a negative effect on the biological activity of the protein. As discovered by the present inventors, this was not the case. Indeed, the substitution of glutamic acid at position B14 with Asp resulted unexpectedly in retention or even increase of biological activity.

The biological activity and/or utility of the relaxin analogs or derivatives of the present invention may be determined using assays known in the art for detecting relaxin activity. For example, bioassays used for the measurement of active relaxin during pregnancy and non-pregnancy, as described in Steinetz et al., 1960, *Endocrinology* 67:102–115 and Sarosi et al., 1983, *American Journal of Obstetrics and Gynecology* 145:402–405, may be used.

Similarly, specific immunoassays to detect for the presence of proteins having relaxin-like immunoactivity can also be used. See e.g., Sherwood et al., 1975, *Endocrinology* 107:691–696; O'Bryne and Steinetz, 1976, *Proceedings of the Society for Experimental Biology and Medicine* 152:272–276. The presence and activity of synthetic analogs of human relaxin comprising one or more accessible tyrosines (permitting direct iodination) may also be tested using a radioimmunoassay (RIA). Eddie et al., 1986, *Lancet* 1:1344–1346.

Each of the above-described assays, however, are limited in their application. Thus, as set forth below and as described in more detail in a co-pending applications, filed concurrently herewith and entitled "Relaxin Diagnostic Assays And Kits," and "Relaxin-Like Factor and Methods And Uses Thereof," additional assays may also be used to assay relaxin analogs to determine the protein's activity and preferred applications.

5.2. Production of Relaxin Analogs and Derivatives

Relaxin analogs may be produced using techniques previously disclosed as useful in producing relaxin and relaxin-like factor. For example, the cDNA of the relaxin analog Asp(B14) may be used to recombinantly produce the relaxin analog according to processes previously described as useful in recombinantly manufacturing relaxin (e.g., U.S. Pat. Nos. 4,758,516, 4,871,670, 4,835,251 and co-pending U.S. Ser. Nos. 07/908,766 (PCT US90/02085) and 08/080,354 (PCT US94/0699)). Alternatively, relaxin analogs and derivatives may be produced recombinantly using, for example, site directed mutagenesis techniques as set forth in Tsurushita, et al., 1988, *Gene* 62:135–139 wherein the Glu at (B14) is mutated to be Asp.

The disclosed sequence information for relaxin may be used also to synthesize the relaxin analog Asp(B14) according to the methods of Bullesbach and Schwabe, 1991, *J. Biol. Chem.* 266:10754–10761, for synthesizing relaxin.

5.3. Indications/Methods of Use

In vitro, proteins having relaxin-like activity decreases collagen synthesis by human dermal and synovial fibroblasts upregulated to overexpress collagen with transforming growth factor-beta (TGF-beta) or interleukin-1, and by fibroblasts constitutively overexpressing collagen obtained from scleroderma patients. For example, relaxin decreases collagen accumulation in vivo in two rodent models of fibrosis. Relaxin, relaxin analogs and derivatives also increase the secretion of the collagenolytic metalloproteinase, collagenase, and down-regulates the expression of the metalloproteinase inhibitor, tissue inhibitor of metalloproteinases.

Relaxin has been implicated consequently in the treatment and diagnosis of various diseases and disorders. For example, studies provide evidence that relaxin is effective in the treatment of scleroderma, sinus bradycardia, cardiovascular disease, neurodegenerative and neurologic disorders, hair loss, depression. See e.g., U.S. Pat. No. 5,166,191; U.S. Ser. No. 07/902,637 (PCT US92/069); U.S. Applications entitled "Method For Treatment Of Hair Loss" and "Method For Treatment Of Depression," both of which are filed concurrently herewith. Evidence also suggest the use of relaxin in diseases and disorders related to the abnormal expression of collagen or fibronectin, such as rheumatoid arthritis.

The relaxin analog provided by the instant invention binds to the relaxin receptor and possesses relaxin-like biological activity and is therefore similarly implicated in the above-identified disease states. Moreover, to the extent that the relaxin analog Asp(B14) retains biological activity which may even be increased compared to wildtype relaxin and RLF, it is also indicated for the treatment of the above-identified diseases.

5.4. Pharmaceutical Dosage Requirements, Formulations and Routes of Administration The following dosage requirements, formulations and routes of administration for relaxin analogs and derivatives are discussed below:

5.4.1. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide serum levels of the active moiety which are sufficient to maintain the relaxin-like activity and effects.

Administration of relaxin analogs and derivatives, alone or in combination with relaxin, can be via any of the accepted modes of administration for agents that serve similar utilities, preferably by systemic administration.

While human dosage levels for treating many of the above-identified relaxin-related diseases or disorders have yet to be optimized for relaxin analogs and derivatives, administered alone or in combination with relaxin, generally, a daily dose is from about 0.05 to 500.0 µg/kg of body weight per day, preferably about 5.0 to 200.0 µg/kg, and most preferably about 10.0 to 100.0 µg/kg, depending on whether the relaxin analog or derivative is administered alone or in combination with relaxin. Generally it is sought to obtain a serum concentration of the relaxin analog or derivative, alone or in combination with relaxin, approximating or greater than normal circulating levels in pregnancy, i.e., 1.0 ng/ml, such as 1.0 to 20 ng/ml, preferably 1.0 to 20 ng/ml.

For administration to a 70 kg person, the dosage range would be about 7.0 µg to 3.5 mg per day, preferably about 42.0 µg to 2.1 mg per day, and most preferably about 84.0 to 700.0 µg per day. The amount of the relaxin analog or derivative administered will, of course, be dependent on the subject and the severity of the affliction, the manner and schedule of administration and the judgment of the prescribing physician and the biological activity of such analog or derivative. One treatment regimen can employ a higher initial dosage level (e.g., 100 to 200 µg/kg/day) followed by decreasing dosages to achieve steady relaxin or relaxin-like serum concentration of about 1.0 ng/ml. Another treatment regimen, particularly postpartum depression, entails administration of an amount of relaxin sufficient to attain normal pregnancy levels of relaxin (about 1.0 ng/ml) followed by gradual decreasing dosages until relaxin serum levels are no longer detectable (e.g. less than about 20 picograms/ml), optionally discontinuing treatment upon reaching that dosage level.

In employing a relaxin analog or derivative, either alone or in combination with relaxin or another relaxin-agent, for treatment of the above conditions, any pharmaceutically acceptable mode of administration can be used. Relaxin analogs and/or their derivatives can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Such proteins can also be administered in sustained or controlled release dosage forms (e.g., employing a slow release bioerodable delivery system), including depot injections, osmotic pumps (such as the Alzet implant made by Alza), pills, transdermal (including electrotransport) patches, and the like, for prolonged administration at a predetermined rate, preferably in unit dosage forms suitable for single administration of precise dosages. The compositions will typically include a conventional pharmaceutical carrier or excipient and relaxin analogs or derivatives. In addition, these compositions may include other active agents, carriers, adjuvants, etc.

In a preferred aspect of the invention, a sustained/controlled release relaxin analog or derivative formulation was a selectively permeable outer barrier with a drug dispensing opening, and an inner relaxin-containing portion designed to deliver dosage of the relaxin analog progressively diminishing at a predetermined rate (e.g. containing about 30 mg of RLF in a matrix for delivery of initially about 500 µg per day diminishing as a rate of 10 µg per day.

In another preferred aspect of the invention, a sustained/controlled release of one or more relaxin analogs or derivatives has a selectively permeable outer barrier with a drug dispensing opening, a first inner relaxin-containing portion designed for steady state release of relaxin at a therapeutically effective daily dosage (e.g. containing about 50 mg of relaxin in a matrix for continuous delivery of about 500 µg per day), and a second inner relaxin analog or derivative a portion designed to deliver a dosage of RLF progressively diminishing at a predetermined rate (e.g. containing about 3 mg of relaxin in a matrix for delivery of initially about 500 µg per day diminishing at a rate of 50kg per day) commencing upon exhaustion of the relaxin from the first inner portion.

Generally, depending on the intended mode of administration, the pharmaceutically acceptable composition will contain about 0.1% to 90%, preferably about 0.5% to 50%, by weight of RLF, either alone or in combination with at least one relaxin analog or derivative, the remainder being suitable pharmaceutical excipients, carriers, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The formulations of human relaxin described in U.S. Ser. No. 08/050,745 are particularly preferred.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.4.2. Routes of Administration

Suitable routes of administration may, for example, include oral, rectal, transmucosal, or intestinal administration. Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

A more recently devised approach for parenteral administration employs the implantation of a slow-release or sustained-release system, such that a constant level of dosage is maintained. See, e.g., U.S. Pat. No. 3,710,795.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

5.4.3. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Formulations of comprising one or more relaxin analogs, derivative or relaxin analog may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of relaxin analog, alone or in combination with relaxin in the present invention.

Relaxin analog for treatment of such disorders such as alopecia, may also be administered topically in a formulation adapted for application to the scalp, such as a shampoo (e.g., as disclosed in U.S. Pat. No. 4,938,953, adapted according to methods known by those skilled in the art, as necessary for the inclusion of protein ingredients) or a gel (e.g., as disclosed in allowed U.S. Ser. No. 08/050,745) optionally with increased relaxin concentrations to facilitate absorption.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

5.4.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of depression, sinus bradycardia, hair loss, neurologic or neurodegenerative diseases, scleroderma, cardiovascular disease or disorders or diseases related to uncontrolled or abnormal collagen or fibronectin formation.

More specific dosage, formulation and methods of administration may be derived from information contained in U.S. Pat. No. 5,166,191, U.S. application Ser. Nos. 07/902,637 (PCT US92/06927) and 08/050,745 (allowed), and co-pending applications, filed concurrently herewith, entitled "Method Of Treatment For Hair Loss" and "Method of Treatment For Depression."

6. EXAMPLES

The following preparations and examples are given to enable those skilled in the art to more clearly understand and to practice the present invention. They should not be considered as limiting the scope of the invention, but merely as being illustrative and representative thereof.

6.1. Relaxin Analog Synthesis and Confirmation of Synthesized Protein

As described above, relaxin analog may be produced by synthesizing the protein based on the relaxin analog's amino acid sequence and/or recombinantly manufacturing the protein.

One procedure for synthesizing relaxin analog is as follows:

Materials. L-Amino acid derivatives for peptide synthesis are purchased either from Bachem Bioscience (Philadelphia, Pa.) or Bachem California (Torrance, Calif.). Solvents for peptide synthesis and chromatography are distilled in glass (Burdick and Jackson; Muscagon, Mich.), and the chemicals for peptide synthesis are obtained from Perkin Elmer Applied Biosystems (Foster City, Calif.). Other chemicals of analytical grade are used without further purification.

Methods. The following method is followed to synthesize relaxin analog:

Peptide Synthesis: The B chain of the relaxin analog protein is synthesized by tert.butyloxycarbonyl[1]-chemistry using conventional HF-labile side chain-protecting groups for all three functional amino acids except cysteines. Cysteine B10 is protected by the acetamidomethyl group and B23 by the thiol-protecting/activating group [S-(3-nitro-2-pyridinesulfenyl)] (CysB23). Methionine is protected by sulfoxide formation, and trytophan by the N(in)formyl group. The synthesis is performed on an Applied Biosystems peptide synthesizer model 430A on [4-(oxymethylphenylacetamidomethyl]resin loaded with 0.4 mmol tert.butyloxycarbonyl-alanine. Deprotection and removal from the solid support is accomplished by HF-treatment in the presence of 5% m-cresol. The crude peptide is extracted with 20% acetic acid and lyophilized. The B chain is purified on Sephadex G50-sf (2.5 cm×50 cm) in 1M acetic acid (yield:840 mg), followed by preparative HPLC on Synchropak RP-P (2.1 cm×25 cm) in portions of 50 to 70 mg. The mobile phase consists of 0.1% trifluoroacetic acid (TFA) in water (solvent A) and 0.1% TFA in 80% acetonitrile (solvent B). The column is equilibrated in 20% B and the peptide is eluted with a linear gradient of 20% B to 50% B over 1 h at a flow rate of 5 ml/min.

The A chain (0.25 mmol) is synthesized via Fast-moc chemistry on an ABI peptide synthesizer (model 430A) on p-benzyloxybenzyl resin. Unlike the synthesis of the B-chain, methods for A-chain synthesis for the relaxin analog is identical to methods used to synthesize relaxin. Specifically, all side chains are protected by TFA-abile protecting groups except Cys(A11), which is acetamidomethyl-protected, and Cys (A24) which is protected by the HF-labile p-menthylbenzyl group. The A chain is deprotected with TFA/thiophenol (10:1 v/v), using 50 mg peptidyl resin/ml for 90 min at room temperature. The TFA is evaporated and the peptide precipitated with ether. The precipitate is collected by centrifugation, the supernatant is discarded, and the pellet is washed twice with ether and air-dried. The peptide is suspended in water, dissolved by the addition of ammonia, and desalted on Sephadex G25-m in 50 mM $NH_4HCO_3$. To the eluate (100 ml) 50 ml of $Me_2SO$ is added in order to accelerate the oxidation of the intrachain disulfide bond A10–A15. The progress of oxidation is observed by the Ellman reaction. After completion of the disulfide bond formation the A chain is dialyzed against water and lyophilized (yield 372.3 mg). Aliquots of 20 mg are further purified by preparative HPLC on Synchropak RP-P (10 mm×250 mm), using 0.1% TFA in water for solvent A and 0.1% TFA in 80% acetonitrile for solvent B. The column is equilibrated in 30% B and the peptide eluted with a linear gradient of 30% B to 50% B over 30 min at a flow rate of 3 ml/min.

For chain combination, 33.4 mg (11.3 µmol) of the A chain(acetamidomethylA10, 4-methylbenzylA24) is treated with 4 ml of HF in the presence of 200 µl of m-cresol for 45 min at 0° C. Thereafter the HF is evaporated in a stream of nitrogen and the peptide precipitated with ether. The pellet is collected and dried over KOH in vacuo for 30 min. The monothiol A chain is dissolved in 4 ml of 8M guanidinium-chloride in 0.1M acetic acid at pH 4.5 and added to 36.3 mg (9.6 µmol) of the B chain. The disulfide bond A24/B23 is formed at 37° C. for 24 h and the resulting product separated first on Sephadex G50-sf in 1M acetic acid (column 2.5 cm×50 cm) (yield 48.7 mg, 78.3%), followed by preparative HPLC on Synchropak RP-P (10 mm×250 mm) using 0.1% TFA in water for solvent A and 0.1% TFA in 80% acetonitrile for solvent B. The column is equilibrated in 30% B and the peptide eluted with a linear gradient of 30% to 45% B over 30 min at a flow rate of 3 ml/min.

The resulting peptide contains acetamidomethyl groups in positions Cys A11 and Cys B10, the N(in) formyl group in Trp B27, and a sulfoxide in the side chain of Met B5. For the formation of the third disulfide bond the peptide is dissolved in water and added to a stirred solution consisting of acetic acid 6N HCl, and 50 mM iodine in acetic acid. The reaction is performed at room temperature for 10 min, quenched with ascorbic acid, and the product is desalted on Sephadex G25-sf in 1M acetic acid and lyophilized. After purification by preparative HPLC (conditions as before), the protein still contained protecting groups in Trp (B27) and Met (B5).

Complete deprotection is achieved first by treatment of 11.3 mg of the peptide with 2 ml of water/piperidine 9:1 (v/v) for 2 min at room temperature. The base is neutralized with 0.4 ml acetic acid and the peptide purified by preparative HPLC, dried, and 10 mg of peptide-containing methionine sulfoxide is reduced with 1 ml of TFA/0.5M $NH_4I$ in water 9:1 v/v for 15 min at 0° C. Free iodine is reduced with 0.5M ascorbic acid in water and the reaction quenched by dilution with water. The final peptide is recovered by preparative HPLC (conditions as before).

The mobile phase of all HPLC systems used consists of 0.1% trifluoroacetic acid in water (solvent A) and 0.1% trifluoroacetic acid in 80% acetonitrile (solvent B).

For preparative HPLC, a Waters HPLC system consisting of two pumps (model 6000A) and gradient programmer (model 680) is used in combination with a Synchropak RP-P column (C18) (SynChrom, In) and an Uvicord S UV (226 nm) monitor (LKB, Bromma Sweden). Usually 1 to 20 mg of peptide is separated using linear gradients as indicated.

The analog's identity is confirmed using analytical HPLC, amino acid analyses, UV spectroscopy, circular dichroism and mass spectrometry.

Alternatively, analogs were synthesized according to the following protocol:

A-Chain Synthesis: The A-chain was synthesized according to the procedure set forth in J. Biol. Chem. 266:10754–10761, 1991.

Asp(B14) B-Chain Synthesis: The B-chain, having an Asp at B14, was synthesized according to the method used to synthesize the A-chain.

Chain Combination: Chain combination was achieved using the protocol essentially set forth in J. Biol. Chem. 266:10754–10761, 1991.

More specifically, 34.5 mg of the A chain was HF deprotected, dissolved in 4 ml of saturated guanidinium chloride containing 0.1M acetic acid at pH 4.5 and added to 48.5 mg of the B chain.

The reaction was performed for 24 h at 37° C. followed by separation on Sephadex G50 at 20% acetic acid. The fractions 13–17 were pooled, lyophilized and further purified by HPLC.

The third disulfide link was synthesized by direct oxidation of the Cys(Acm) groups with iodine in 70% acetic acid, the reaction quenched with ascorbic acid, diluted to about 20% of acetic acid and purified by preparative HPLC. The tryptophan side chain was removed by treatment with NaOH and the peptide recovered by HPLC. At last the methionine sulfoxide was reduced with ammonium iodide in 90% TFA, quenched by the addition of water and ascorbic acid and purified by HPLC. yield 1.07 mg.

This protocol may be modified further as follows:

a) 40 mg of A and 55 mg of the B chain were combined for 6 h at 37° C.

b) The tryptophan side chain protecting groups were removed with 10% piperidine in water for 2 minutes at room temperature.

Such modification yielded approximately 3.6 mg of product.

6.2. Production of Labeled Relaxin Analog $^{125}$I-labeled relaxin analog, containing side chain-protected tryptophan and methionine, may be prepared according to the above procedure wherein the synthesized peptide (10 μg in 5 μl of water) is then placed into a 200 μl Eppendorf vial and 5 μl phosphate buffer (250 mM, pH 7.4), followed by 2 μl of $^{125}$I-(1 mCi), and 5 μl of chloramine T (2 mg/ml in phosphate buffer pH 7.4) are added. The reaction is performed for 1 min on ice, quenched by addition of 5 μl of sodium thiosulfate (5 H$_2$O) (50 mg/ml in phosphate buffer pH 7.4), and 5 μl of NaI (20 mg/ml in phosphate buffer pH 7.4). The side chain-protecting group of Trp is removed by addition of 5 μl of piperidine. After 2 minutes at room temperature the reaction is quenched by the addition of 5 μl of glacial acid, the reaction mixture is diluted with 10 μl of water and loaded onto a Aquapore 300 column for separation. The protein is detected by UV absorbance and peaks are manually collected into 100 μl of 1% bovine serum albumin in water.

The labeled relaxin analog may be used as an relaxin analog tracer which could then be used to separate by HPLC the different relaxin derivatives to yield a carrier-free tracer. Alternatively, such labeled relaxin analog may also be used in binding assays and for relaxin receptor mapping.

6.3. Relaxin Analog-Binding Assays

Relaxin analog-binding assays are performed as described in Yang, et al., 1992, *Endocrinology* 130:179–185 and Bullesbach, et al., 1994, *Endocrine* 2:1115–1120, using crude membrane preparations of mouse tissue. Mouse brains of 2 mice are collected into 15 ml of chilled buffer (25 mM HEPES, 0.14M NaCl, 5.7 mM KCl, 0.2 mM phenylmethylsulfonyl-fluoride, and 80 mg/ml soybean trypsin inhibitor, pH 7.5) supplemented with sucrose (0.25M, final concentration). The tissue is then homogenized on ice for 10 s with a Polytron homogenizer (Brinlmann, Westbury, N.Y.) at setting 5. The homogenate is centrifuged at 700 rpm for 10 min at 4° C. and the supernatants are recentrifuged at 10,000×g for 1 h. The pellet is then resuspended in 15 ml of ice cold binding buffer, 25 mM HEPES, 0.14M NaCl, 5.7 mM KCl, 0.2 mM phenylmethylsulfonylfluoride, and 80 mg/ml soybean trypsin inhibitor, pH 7.5, supplemented with 1% bovine serum albumin, and centrifuged for 1 h at 10,000×g. The crude membrane preparation is suspended in 1 ml of binding buffer and 40 μl is used per assay. The assay is performed using 40 μl of tracer (about 100,000 cpm of porcine relaxin tracer=150 pM) and 20 μl of relaxin analog at various concentrations. The assay is incubated for 1 h at room temperature, and the suspension is diluted with 1 ml of wash buffer (25 mM HEPES, 0.14M NaCl, 5.7 mM KCl, 1% bovine serum albumin, 0.01% NaN$_3$) and centrifuged in Eppendorf centrifuge at 14,000 rpm for 10 min. The supernatant is discarded, the tip of the vial cut and counted in a gamma-counter. Nonspecific binding is determined in the presence of 2 μl/ml of unlabeled competitor (0.33 μM).

Tissue specificity was determined using crude membrane preparations of leg muscles, kidneys, liver. brain, and uterus (of estrogen primed mice). The crude membranes are prepared as described for relaxin. Binding is based on protein concentration determined by Lowry.

According to the above-described assay, relaxin analogs displaces the relaxin tracer from a mouse brain relaxin receptor preparation.

6.4. Sperm Motility Assay

Relaxin analogs and derivatives having relaxin-like activity may be identified by a sperm motility assay.

Materials And Methods. Semen is obtained by masturbation from healthy volunteers. The sample is allowed to liquefy at room temperature and is then mixed with Minimum Essential Medium (MEM) with Hepes buffer added. This medium is used because it coincides with that washing medium employed by the in vitro clinic at MUSC. The sperm is then separated from the seminal fluid and MEM by centrifugation. The resultant sperm pellet is then resuspended in MEM at room temperature. Aliquots are then place in siliconized centrifuge tubes and one of several compounds added: 1) human relaxin 10 ng/ml, 2) human relaxin 100 ng/ml, 3) relaxin analog 10 ng/ml, 4) relaxin analog factor 100 ng/ml, 5) one fraction of alkaline gland fluid from stingrays diluted 1:8 with pentoxyfyline. The additive is mixed well with the sperm/medium mixture. Samples are taken at 0, 2, 4, 6 and 24 hour intervals for automated determination of the following parameters: 1) motility, 2) progressivity, 3) path velocity, 4) progressive velocity, 5) track speed, 6) elongation, 7) lateral displacement, 8) cross beat frequency, 9) straightness, 10) linearity. Briefly described, each sample is loaded into a Maker heated specimen chamber and viewed in a light microscope equipped with laser doppler optics (IVOS, Beverly, Mass.). Sample readings taken at approximately 3 minutes and results are displayed in hard copy form.

Experimental Results. Relaxin analogs added to washed human sperm preserve the motility compared to untreated controls in which motility and thus potential fertilizing capacity significantly declines over time.

6.5. In Vitro Inhibition of Collagen Expression By Human Synovial Fibroblasts Whether relaxin analogs inhibit collagen expression has been studied in the context of human synovial fibroblasts. Specifically, relaxin analog (1–100 ng/ml) is applied to human synovial fibroblasts in serum-free medium and assayed for collagen secretion by biosynthetic labelling with $^3$H-proline in the presence of ascorbate and B-aminopropionitrile. When tested on fibroblasts stimulated with TGF-beta, relaxin analog ability to inhibit collagen expression at various dose levels can be determined.

6.6. Assay to Determine the Inhibition of Collagen Expression

The method for detecting and measuring collagen formation in the presence of relaxin described in Unemori and Amento, 1990, *J. Biol. Chem.* 265:10681–685 has been modified as follows to determine the ability of relaxin analog, in vitro, to modulate the expression of collagen.

Materials And Methods. Rheumatoid synovial fibroblasts (Strain No. RSF64) are seeded at a density of 6.25×10$^4$ cells/cm$^2$ in tissue culture dishes in Dulbecco's Modified Eagle's Medium (DMEM) supplemented with 10% fetal bovine serum. After 24 hours, the cells are washed and treated with DMEM supplemented with 0.2% lactalbumin hydroxylsate with relaxin, relaxin analog and/or transforming growth factor (TGF-β).

The cells are simultaneously biosynthetically labelled with $^3$H=proline (25 µCi/ml) in the presence of ascorbate and BAPN. After 24 hours, the conditioned media is collected and electrophoresed on 4–12% polyacrylamide gels (NOVEX) under reducing conditions. Gels is enhanced, dried, and exposed to X-ray films for 1–2 weeks. Collagen bands is identified on the X-ray films as bacterial collagenase-sensitive, proline-incorporating bands between 95–200 kDa. Band density is quantified by scanning densitometry and used as estimates of collagen expression.

Experimental Results. Using the above protocol, the relaxin analog decreased TGF-β induced collagen overexpression independently by 25% when used at 100 ng/ml.

6.7. In Vitro Stimulation of Procollagense Expression by Synovial Fibroblasts A method for detecting and measuring procollagenase formation is described in Unemori, et al., 1991, *J. Biol. Chem.* 266:23477–482. Such method was modified to measure the expression of procollagenase in the presence of one or more relaxin analogs as follows:

Materials And Methods. Rheumatoid synovial fibroblasts (Strain No. RSF112) is seeded at a density of $6.25 \times 10^4$ cells/cm$^2$ in tissue culture dishes in DMEM supplemented with 10% fetal bovine serum. After twenty-four hours, the cells are washed and treated with DMEM supplemented with 0.2% lactalbumin hydroxylate with relaxin at 1, 10 and 100 ng/ml for 48 to 72 hours. Conditioned media is collected and an aliquot analyzed by gelatin zymography. Procollagenase is identified as a gelatinlytic doublet at 52/57 kDa. The intensity of the doublet (i.e., the amount of procollagenase expressed) is quantified by scanning densitometry.

Experimental Results. Relaxin analog stimulates expression of procollagenase in a dose-dependent manner.

6.8. Cyclic AMP Assay

The cAMP assay is a competitive immunoassay commercially available through Amersham Corporation.

Materials and Methods. To determine cAMP release induced by relaxin analog, normal human endometrial cells are grown at $1.2 \times 10^4$ cells/well in a 96-well plate in DMEM/F12+10% newborn calf serum. 24 hours later, the cells are washed in serum-free medium comprised of DMEM/F12+0.2% lactalbumin hydrolysate. 24 hours later, the cells are treated with relaxin and/or relaxin analog in the presence of isobutylmethylxanthine and forskolin for 30 min. The cell lysates are harvested with 0.1N HCL, neutralized with 0.1N NaOH, then assayed in the immunoassay (Amersham Corp).

Experimental Results. When relaxin was assayed at 0.78 ng/ml, 86 pM cAMP was measured in endometrial cell lysates. When relaxin analog (2.5 ug/ml) was simultaneously added, 470 pM cAMP, roughly a 5-fold enhancement in cAMP production, was measured. When a relaxin concentration of 3.12 ng/ml was tested with and without relaxin analog (2.5 ug/ml), enhancement was measurable with relaxin+relaxin analog as compared with relaxin alone.

6.9. Mouse Symphysis Pubis Assay

Mouse interpubic ligament assays were performed essentially as described by Steinetz, et al., 1960, *Endocrinology* 67:102–115 as modified as follows:

Ovariectomized virgin female mice were printed with 5 µg estrogen cypionate in 100 µl sesame oil. Five days later the mice were injected subcutaneously with human relaxin, relaxin analog Asp(B14), and the control mutants Ser(A10)/Ser(A15) [=Ser$_2$], Ala(A10)/Ala(A15) [=Ala$_2$], des (B1–4), and Gln(B14) in 100 µl of 0.1% benzopurpurin 4B. Specifically, groups of five animals received either human relaxin or relaxin analogs at a dose of 0.2 µg, 0.5 µg and 1.0 µg. For negative control 100 µl of 0.1% benzopurpurin 4B in water were injected. After 16 hours the mice were killed in an atmosphere of $CO_2$, the symphysis pubis dissected free, and the distance between the interpubic bones measured with a dissecting microscope fitted with transilluminating fiber optics.

Figure 1A:
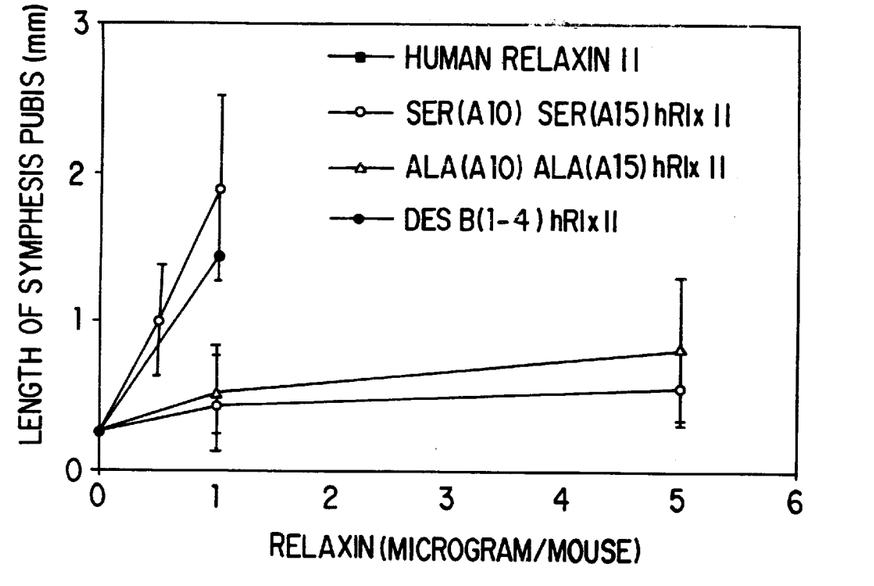
FIGS. 1A and B show the relaxin analog ASP(B14) is significantly higher biological activity than wild type relaxin.
Figure 1B:
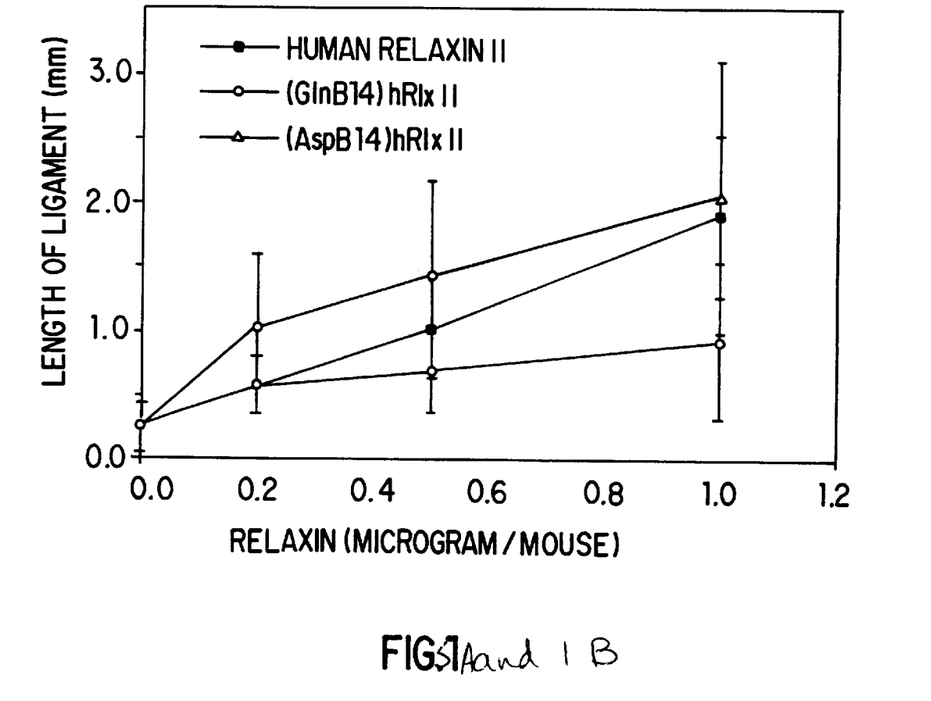

In the experiment set forth in Table 1 and depicted in FIGS 1(A&B), the relaxin analog Asp(B14) showed significantly higher biological activity than wild type relaxin. Specifically, 0.5 µg Asp(B14) exhibited 1.43-fold activity compared to wildtype relaxin, at 1.0 µg the biological activity of the Asp(B14) analog was still almost 1.1-fold compared to the wildtype hormone. All control mutants tested in this assay, i.e. Ser(A10)/Ser(A15) [=Ser$_2$], Ala(A10)/Ala(A15) [=Ala$_2$], des (B1–4), and Gln(B14), had significantly lower biological activity than both wildtype relaxin and the high activity analog Asp(B14).

TABLE I

Mouse Symphysis Pubis Assay

| A. Animal # | Bp | 0.5 µg hR1x | 1 µg hR1x | 1 µg Ser2 | 5 µg Ser2 | 1 µg Ala2 | 5 µg Ala2 |
|---|---|---|---|---|---|---|---|
| 1 | 0.14 | 0.86 | 1.72 | 1.00 | .29 | .57 | 1.43 |
| 2 | .14 | 1.57 | 2.86 | .29 | .86 | .29 | .72 |
| 3 | .29 | 0.86 | 1.72 | .43 | .72 | .29 | .43 |
| 4 | .14 | 1.14 | 1.14 | .14 | .29 | .43 | .29 |
| 5 | .57 | 0.57 | 2.00 | .29 | .57 | 1.00 | 1.14 |
| Mean | 0.26 | 1.00 | 1.89 | 0.43 | 0.55 | 0.52 | 0.80 |
| Std. Dev. | 0.19 | 0.38 | 0.63 | 0.33 | 0.26 | 0.29 | 0.48 |
| Significance based on Bp | — | 0.004 | 0.001 | 0.340 | 0.075 | 0.134 | 0.045 |

| B. Animal # | 0.2 µg Gln B14 | 0.5 µg Gln B14 | 1 µg Gln B14 | 0.2 µg Asp B14 | 0.5 µg Asp B14 | 1 µg Asp B14 | 1 µg desB(1–4) |
|---|---|---|---|---|---|---|---|
| 1 | 0.72 | 0.29 | 0.29 | 0.57 | 0.72 | 0.86 | 1.72 |
| 2 | 0.86 | 0.57 | 1.57 | 1.00 | 2.00 | 1.86 | 1.14 |
| 3 | 0.29 | 0.57 | 1.43 | 0.43 | 2.00 | 2.00 | 1.57 |

TABLE I-continued

| Mouse Symphysis Pubis Assay | | | | | | | |
|---|---|---|---|---|---|---|---|
| 4 | 0.57 | .86 | 0.29 | 1.72 | 0.57 | 3.43 | 1.29 |
| 5 | 0.43 | 1.14 | 1.00 | 1.43 | 1.86 | | 1.43 |
| Mean | 0.57 | 0.69 | 0.92 | 1.03 | 1.43 | 2.04 | 1.43 |
| Std. Dev. | 0.23 | 0.32 | 0.61 | 0.55 | 0.72 | 1.06 | 0.23 |
| Significance based on Bp | 0.042 | 0.033 | 0.049 | 0.018 | 0.008 | 0.007 | 0.000 |

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety. In addition, the publications listed below are of interest in connection with various aspects of the invention and are incorporated herein as part of the disclosure:

1. Adham et al., 1993, *J. Biol. Chem.* 268:26668–26672;
2. Adler et al., 1973, *Methods Enzymol.* 27:675–735;
3. Büllesbach et al., 1994, *Endocrine.* 2:1115–1120;
4. Büllesbach and Schwabe, 1994, *J. Biol. Chem.* 269:13124–13128;
5. Büllesbach and Schwabe, 1993, *Biochem. Biophys. Res. Commun.* 196:311–319;
6. Büllesbach and Schwabe, 1992, *J. Biol. Chem.* 267:22957–22960;
7. Büllesbach and Schwabe, 1991, *J. Biol. Chem.* 266:10754–10761;
8. Büllesbach et al., 1980, *Hoppe Seyler's Z. Physiol. Chem.* 361:865–873;
9. Burkhardt et al., 1994, *Genomics* 20:13–19;
10. Eigenbrot et al., 1991, *J. Mol. Biol.* 221:15–21;
11. Ellman, 1959, *Arch. Biochem. Biophys.* 82:70–77;
12. Hock and Hollenberg, 1980, *J. Biol. Chem.* 255:10731–10736;
13. Linde et al., 1986, *J. Chromatogr.* 369:327–339;
14. Olefsky et al., 1982, *Ann. N.Y. Acad. Sci.* 380:200–216;
15. Rembiesa et al., 1993, *Endocrine J.* 1:263–268;
16. Schwabe and Büllesbach, 1994, *FASEB J.* 8:1–2;
17. Schwabe and Harmon, 1978, *Biochem. Biophys. Res. Commun.* 84:374–380;
18. Sieber et al., 1977, *Helv. Chim. Acta* 60:27–37;
19. Steinetz et al., 1960, *Endocrinology* 67:102–115;
20. Tam et al., 1991, *J. Am. Chem. Soc.* 113:6657–6662;
21. Tashima et al., 1995, *J. Clin. Endocrinal. Metab.* 80:707–710; and
22. Yang et al., 1992, *Endocrinology* 130:179–185.

What is claimed:

1. Relaxin analog comprising an A chain and a B chain, said A chain having the amino acid sequence:

Gln-Leu-Tyr-Ser-Ala-Leu-Ala-Asn-Lys-Cys-Cys-His-Val-Gly-Cys-Thr-Lys-Arg-Ser-Leu-Ala-Arg-Phe-Cys (SEQ ID NO:2)

or an amino acid sequence truncated by up to about 6 amino acids from the N-terminus and/or by up to 6 amino acids from the C-terminus;

said B chain having the amino acid sequence:
Asp-Ser-Trp-Met-Glu-Glu-Val-Ile-Lys-Leu-Cys-Gly-Arg-Asp-Leu-Val-Arg-Ala-Gln-Ile-Ala-Ile-Cys-Gly-Met-Ser-Thr-Trp-Ser or an amino acid sequence truncated by up to 5 amino acids from the N-terminus and/or by up to 5 amino acids from the C-terminus;

said A and B chains linked by disulfide bonds between A11 and B11 and wherein said relaxin analog displaces bound relaxin tracer from the receptor to which it is bound.

2. The relaxin analog of claim 1 wherein 0 up to about 6 amino acids are deleted from the 5' end and 0 up to about 6 amino acids are deleted from the 3' end of the A-chain.

3. The relaxin analog of claim 1 wherein 0 up to about 5 amino acids are deleted from the 5' end and 0 up to about 5 amino acids are deleted from the 3' end of the B-chain.

4. A method of treating a mammal for a condition susceptible to treatment with relaxin, comprising administering to a mammal in need thereof a therapeutically effective amount of the relaxin analog of claim 1.

5. The method of claim 4 wherein the disease is selected from the group comprising cardiovascular disease, neurodegenerative or neurologic disease, sinus bradycardia, depression, hair loss, or diseases related to uncontrolled or abnormal collagen or fibronectin formation.

6. The method of claim 5 wherein the disease related to the uncontrolled or abnormal collagen formation is scleroderma.

7. A pharmaceutical composition comprising the relaxin analog of claim 1 and a pharmaceutically acceptable excipient.

8. A pharmaceutical composition of claim 7 wherein the effective amount is 0.05 to 500 μg/kg of body weight per day.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: unknown     ( i i ) MOLECULE TYPE: protein     ( x i ) SEQUENCE DESCRIPTION: SEQ ID NO:1:

```
Asp Ser Trp Met Glu Glu Val Ile Lys Leu Cys Gly Arg Asp Leu Val
1               5                   10                  15

Arg Ala Gln Ile Ala Ile Cys Gly Met Ser Thr Trp Ser
                20                  25
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown (i i) MOLECULE TYPE: protein (x i) SEQUENCE DESCRIPTION: SEQ ID NO:2:

Gln Leu Tyr Ser Ala Leu Ala Asn Lys Cys Cys His Val Gly Cys Thr
1               5                   10                  15

Lys Arg Ser Leu Ala Arg Phe Cys
                20